United States Patent [19]

Austin et al.

[11] 4,209,465

[45] Jun. 24, 1980

[54] DECOMPOSITION OF CUMENE HYDROPEROXIDE USING A STABLE CARBONIUM, TROPYLIUM OR OXONIUM SALT AS THE CATALYST

[75] Inventors: Richard G. Austin, Churchill; Wayne R. Pretzer; Thaddeus P. Kobylinski, both of Gibsonia, all of Pa.

[73] Assignee: Gulf Research and Development Company, Pittsburgh, Pa.

[21] Appl. No.: 50,470

[22] Filed: Jun. 20, 1979

[51] Int. Cl.² ................. C07C 45/00; C07C 37/08
[52] U.S. Cl. .................................... 568/385; 568/798
[58] Field of Search .................. 260/593 A; 568/798

[56] References Cited

U.S. PATENT DOCUMENTS

| 2,628,984 | 2/1953 | Aller et al. | 260/593 A |
| 2,663,735 | 12/1953 | Filar et al. | 568/798 |
| 3,928,477 | 12/1975 | Field et al. | 260/593 A |
| 3,948,995 | 4/1976 | Jouffret | 568/798 |
| 4,075,250 | 2/1978 | Field et al. | 568/798 |

Primary Examiner—Norman Morgenstern
Assistant Examiner—James H. Reamer

[57] ABSTRACT

Cumene hydroperoxide is decomposed to phenol and acetone using an isolable carbonium, tropylium or oxonium salt as the catalyst. Triphenylcarbonium tetrafluoborate catalyzes the decomposition of cumene hydroperoxide to phenol and acetone.

11 Claims, No Drawings

DECOMPOSITION OF CUMENE HYDROPEROXIDE USING A STABLE CARBONIUM, TROPYLIUM OR OXONIUM SALT AS THE CATALYST

FIELD OF THE INVENTION

This invention relates to the catalytic cleavage of cumene hydroperoxide to equal molar portions of phenol and acetone in the presence of a relatively stable, isolable carbonium, tropylium or oxonium salt, such as the tetrafluoborate, as the catalyst.

DESCRIPTION OF THE PRIOR ART

Cumene can be readily oxidized with air to form cumene hydroperoxide and the hydroperoxide can then be decomposed to form equal molar amounts of phenol and acetone. In the commercial process for producing phenol by this general method, a small amount of a mineral acid, generally sulfuric acid, is used as the decomposition or cleavage catalyst. Since phenol and acetone are the products of the cleavage reaction, the reaction solvent can conveniently be a phenol-acetone solution. In this process the cumene hydroperoxide instantaneously decomposes to phenol and acetone as it is slowly added in solution with cumene to the mineral acid solution. The highly exothermic reaction is controlled by the rate of cumen hydroperoxide addition and by acetone reflux. Water is substantially excluded from the reaction medium during the decomposition reaction to insure homogeneity. These processing details are essentially described in U.S. Pat. No. 2,663,735.

DESCRIPTION OF THE INVENTION

The desired decomposition of cumene hydroperoxide is a cleavage to equal mols of phenol and acetone, that is, about 62 weight percent phenol and 38 weight percent acetone. In using sulfuric acid as the decomposition catalyst, a selectivity to phenol of about 85 to 95 percent is generally obtained. The non-selective decomposition product particularly as catalyzed by a strong mineral acid includes cumyl alcohol, acetophenone, methylbenzofuran, several organic acids, mono- and dicumylphenol, diacetone alcohol, acetol, mesityl oxide, phorone, alpha-methylstyrene and various oligomers of alpha-methylstyrene which are tar-like substances. When the reaction product is distilled, these by-products remain in the residue which is collectively called "tar" or "tars". It has been reported that the main products in this "tar" are cumylphenol and dicumylphenol, the polymers of alpha-methylstyrene, acetophenone and diacetone alcohol. Since few of these by-products of the non-selective reaction can be economically recovered, this non-selective reaction represents a significant economic loss.

A particular advantage in the use of the carbonium, tropylium or oxonium salt decomposition catalysts of this invention is that a selectivity greater than 95 percent, approaching 100 percent under optimum conditions, can be obtained. Another advantage of these catalysts in contrast with the strong mineral acid catalyst is that the catalysts of this invention do not promote the alkylation of phenol product to cumylphenol nor the oligomerization of aromatic olefin to form tars. Furthermore, in the present process the major by-product, if any, alpha-methylstyrene, can be recovered and hydrogenated to cumene for recycle in the process. A further advantage in the use of the present catalysts instead of the mineral acid catalysts is that the corrosion problems of the latter are substantially avoided.

The catalysts of this invention are salts comprising an organic cation selected from triphenylcarbonium $(ph)_3C-$, tropylium $C_7H_7-$ and tri(lower) alkyl oxonium $R_3O-$ and inorganic anions selected from tetrafluoborate—$BF_4$, hexafluorophosphate —$PF_6$, hexachlorostibnate —$SbCl_6$ and hexafluoroarsenate —$AsF_6$. These salts are solids which are readily soluble in the cumene hydroperoxide solution. They can also be dissolved in a solvent such as acetone, cumene, benzene, toluene, and the like, which is inert in the reaction environment, for addition to the reactor. Since these salts are relatively stable, they can be isolated and stored for future use.

We have found that the concentration of the catalyst is an important reaction variable. That is, the higher the catalyst concentration, the more rapid the reaction until too much catalyst renders the exothermic reaction uncontrollable. On the other hand, the reaction is too slow with too little catalyst. Some of the catalysts are active at lower concentrations, while others require higher amounts for a suitable rate of reaction. Within these constraints the concentration of the catalyst can be as low as about 20 parts per million parts of total reaction liquid (ppm.) up to about one percent, or even higher with appropriate control of reaction temperature, and preferably its concentration wil be between about 500 ppm. and about 0.5 percent.

Since the cleavage reaction is highly exothermic, temperature control of the reaction liquid is generally provided. This temperature control can be accomplished by controlling the amount of catalyst used or by controlling the rate at which the catalyst is mixed with the cumene hydroperoxide. But with the highly active catalysts one or both of the following techniques for temperature control is desirably utilized. Temperature control can be effected, in part, by maintaining appropriate means for the positive cooling of the reaction liquid during the reaction such as by solvent reflux or by submerged cooling coils. Another effective and useful method of temperature control is the employment of sufficient inert solvent to serve as a heat sink. The reaction can be carried out within the range of between about 25 to about 110° C. and preferably a range of between about 60 to about 80° C. At the lower temperatures the reaction becomes quite slow although highly selective, while undesirable tar formation can result at higher temperatures due to the effects of thermal decomposition of the cumene hydroperoxide.

The pressure within the reactor is not a critical factor during the decomposition reaction. Generally, the pressure will range from a pressure moderately below to moderately above atmospheric pressure.

The cumene hydroperoxide can desirably be prepared by oxidation of cumene with air in the conventional manner. In this process a solution of at least about 10 weight percent cumene hydroperoxide in cumene is desirably produced, although a product containing less than 10 weight percent cumene hydroperoxide can be utilized. Since it is not particularly desirable to use an excessive amount of cumene in a continuous process as a reaction solvent due to subsequent handling and separation problems, it is preferred that a more concentrated solution of cumene hydroperoxide be prepared. In this oxidation reaction the maximum concentration of cumene hydroperoxide that can conveniently be produced is about 30 percent.

The cumene hydroperoxide to be used in the decomposition reaction can be further concentrated by flashing off sufficient cumene to form a feed solution of between about 60 to about 90 percent, preferably about 65 to about 80 percent, cumene hydroperoxide. Although pure cumene hydroperoxide can be used, it is not desirable to obtain it in this final stage of purity for economic reasons and also for safety reasons since the presence of some cumene tends to stabilize the cumene hydroperoxide. The decomposition reaction can suitably be carried out with as little as about 0.1 weight percent cumene hydroperoxide in the reaction liquid, with at least about 0.5 percent being preferred and at least about 1.0 percent being most preferred. The maximum amount of cumene hydroperoxide in the cleavage reaction liquid will suitably be about 20 weight percent, preferably about 10 percent and most preferably about 5 percent. Since explosions have in the past resulted from cumene hydroperoxide reactions which have run away, it is generally desired to carry out the reaction with substantial diluent as a safety measure, resulting in a concentration of cumene hydroperoxide in the reaction liquid much below the upper limit.

The solvent used in this process can be the cumene associated with the cumene hydroperoxide as described above. However, since phenol and acetone are the desired reaction product, a phenol-acetone solvent is generally desirable in order to simplify product separation. Since a solution of cumene hydroperoxide and cumene is usually added to the reactor, the sovlent system will therefore include cumene as a component, generally a minor component. The solvent can conveniently be the 1:1 molar phenol to acetone product of the cumene hydroperoxide cleavage reaction, however, variations in the relative proportions can be used. Thus, although there is no particular advantage to using an excess of phenol, an excess of acetone may be desirable, particularly if the acetone is to be utilized for temperature maintenance during reaction by means of acetone reflux or boil-off. Therefore, the mol ratio of acetone to phenol as the solvent in the reaction mixture can be as high as about 10:1 and preferably no higher than about 3:1. Other usable solvents include aromatic solvents such as benzene, toluene, and the like; ethers such as diethyl ether and tetrahydrofuran, or any other solvent which is compatible with the reactant and catalyst and can be conveniently separated.

Phenol is not inert when used as a solvent for cumene hydroperoxide in its decomposition. Rather phenol, by virture of its acid nature, has been found to be a catalyst for the decomposition of cumene hydroperoxide in a reaction which is significantly slower than the above-described mineral acid catalyzed reaction. Morever, the selectivity of this phenol catalyzed decomposition of cumene hydroperoxide is very poor, being less than 80 percent selectivity to phenol as determined by a study of the reaction. It is readily apparent that the presence of solvent phenol in the mineral acid catalyzed reaction of the commercial processes is not noticeably detrimental because the great speed of the mineral acid catalyzed decomposition effectively eliminates the detrimental effect on selectivity of the relatively slow phenol catalyzed reaction. In our reaction we can avoid a significant adverse effect on product selectivity from the phenol catalyzed reaction, particularly when phenol is present as an added solvent, by appropriate catalyst selection and/or concentration to obtain a suitably rapid reaction.

When operating under the general conditions described herein, particularly within a temperature range between about 60° and 80° C., the decomposition reaction to substantial completion, as a batch or as a continuous process, will take place in about two minutes to about two hours, and preferably will take place in about five to about 45 minutes. The process can also be carried out in a semi-continuous manner in which the reactant, solvent and catalyst are continuously added to a stirred tank reactor at a rate coinciding with the withdrawal rate, sufficient to provide a suitable average reaction rate within the above time ranges for substantially complete reaction. Since a significant quantity of unreacted cumene hydroperoxide in the final reaction product can undesirably interfere with the distillative separation procedure, it is preferred that there be a substantially complete decomposition of the cumene hydroperoxide in the reaction stage.

DESCRIPTION OF PREFERRED EMBODIMENTS

In the following examples, the hydroperoxide was analyzed by iodometric titration with sodium thiosulfate. The decomposition product resulting from the reactions catalyzed with the catalysts of the present invention was light yellow in color and transparent, indicating very slight tar, while the sulfuric acid catalyzed product liquid was black and opaque. Both the residue and the product distillate were analyzed. The analyses for compounds other than hydroperoxide were accomplished by gas chromatography or by high performance liquid chromatography.

EXAMPLE 1

The catalytic activity of sulfuric acid for the decomposition of cumene hydroperoxide was observed. A 57.3 percent solution of cumene hydroperoxide in cumene was added dropwise into 100 ml. of a two percent solution of sulfuric acid in acetone in a 300 ml. round bottom flask open to the atmosphere. Each drop instantly decomposed as it contacted the solution. Since no positive cooling of the reaction liquid was provided, the temperature of the solution rose from room temperature (about 25° C.) at the beginning of the addition to 44° C. upon the completion of the addition. A total of 35.2 g. of the cumene hydroperoxide was added over 60 minutes. Analysis of the product showed that 99.9 percent of the cumene hydroperoxide had reacted at a selectivity of 93 percent to phenol.

EXAMPLE 2

The following reactions were carried out in a glass reactor equipped with a magnetic stirrer and operated at a pressure within the reactor slightly above atmospheric pressure. The reactor was cooled by a cold finger in the liquid. Small samples of the reaction liquid (about 1 ml.) were periodically withdrawn to monitor the reaction.

Phenol was tested as a decomposition catalyst for cumene hydroperoxide at several temperatures. About 20 g. of a solution consisting of 5 parts phenol, 3 parts acetone and 1 part cumene were placed in the reactor. About 2 ml. of a solution consisting of 55 percent cumene hydroperoxide in cumene were injected into the reactor in each experiment. Table I summarizes the results of these experiments.

Table I

| Minutes | Cumene Hydroperoxide Decomposed, % | | | |
|---|---|---|---|---|
| | 10 | 20 | 50 | 100 |
| Temp. | | | | |
| 40° C. | trace | trace | trace | trace. |
| 60° C. | — | 8 | 19 | 39 |
| 80° C. | 18 | 34 | 60 | 85 |

The experiment at 80° C. was allowed to run for four and one-half hours at which time the cumene hydroperoxide was completely decomposed. Analysis of this product mixture disclosed that it contained 77 percent phenol, 8 percent alpha-methylstyrene, 4 percent acetophenone, 4 percent dimethylbenzyl alcohol, and 7 percent of a residuum consisting of aromatic carbonyls, aromatic alcohols, substituted phenols, substituted benzofurans and methylstyrene oligomers.

EXAMPLE 3

A 200 ml. glass reactor partially immersed in a heated oil bath at 60° C. and equipped with a magnetic stirrer and a cold finger was used in these experiments. The cold finger was cooled with tap water and was only used when necessary to prevent excessive temperatures. The reactor was charged with 22 g. of a 20 percent solution of cumene hydroperoxide (CHP) which heated to 60° C. After the solution had reached a temperature of 60° C.,0.01 g. (455 ppm.) of triphenylcarbonium tetrafluoborate was added to initiate the decomposition reaction. The temperature rose to a maximum temperature of 70° C. and after 30 minutes the reaction was substantially complete. Analysis of the product showed a selectivity of 91 percent to phenol, 4 percent to alphamethylstyrene, 3 percent to acetophenone and 2 percent to α,α-dimethylbenzyl alcohol.

the following experiments were all carried out in the same equipment descirbed in Example 3 using the same amount of the 20 percent cumene hydroperoxide. They differ in the catalyst or amount of catalyst which was added to the cumene hydroperoxide at 60° C., the maximum temperature which occurred and the total reaction time. In all experiments there was greater than 95 percent conversion of the cumene hydroperoxide.

EXAMPLE 4

In this example 0.003 g. (136 ppm.) of triphenylcarbonium tetrafluoborate was added to the cumene hydroperoxide. The temperature rose to a maximum temperature of 91° C. and after one hour the products were removed for analysis. The reaction resulted in a selectivity of 88 percent to phenol, 3 percent to alphamethylstyrene, 5 percent to acetophenone and 4 percent to dimethylbenzyl alcohol.

EXAMPLE 5

A solution containing 0.005 g. of triphenylcarbonium hexafluoroarsenate in 5 ml. of acetone was prepared. A 0.5 ml. portion of this solution was added to the cumene hydroperoxide at 60° C. The temperature rose to a maximum of 81° C. After 45 minutes the product mixture was analyzed. It was determined that the cumene hydroperoxide has reacted at a selectivity of 93 percent to phenol, 3 percent to alpha-methylstyrene, 3 percent to acetophenone and one percent to dimethylbenzyl alcohol.

EXAMPLE 6

After the cumene hydroperoxide reached 60° C., 0.008 g. (346 ppm.) of triphenylcarbonium hexachlorostibnate was added. The temperature reached a maximum value of 90° C. After 30 minutes of reaction time, the reaction product was analyzed. It was determined that the selectivity to phenol was 78 percent, to alphamethylstyrene 12 percent, to acetophenone 7 percent and to dimethylbenzyl alcohol 2 percent.

EXAMPLE 7

In this reaction sufficient tropylium tetrafluorophosphate was added to the cumene hydroperoxide to provide 500 ppm. of the catalyst. The temperature rose to 90° C. After 30 minutes reaction time, analysis of the products showed a selectivity of 77.4 percent to phenol, 20.5 percent to alpha-methylstyrene and 2.1 percent to acetophenone.

EXAMPLE 8

The catalyst tropylium hexachlorostibnate was added to the cumene hydroperoxide in an amount to provide 841 ppm. in the solution. The temperature rose to 90° C. and after 30 minutes the product was analyzed. Analysis showed a selectivity to phenol of 77 percent, to alphamethylstyrene of 3.3 percent, to acetophenone of 5.1 percent and 1.6 percent to dimethylbenzyl alcohol.

EXAMPLE 9

In this experiment 260 ppm. of tropylium tetrafluoborate was added to the cumene hydroperoxide solution. A maximum temperature of 90° C. was reached within five minutes. Analysis showed a selectivity of 90 percent to phenol, 3.3 percent to alpha-methylstyrene, 5.1 percent to acetophenone and 1.6 percent to dimethylbenzyl alcohol.

EXAMPLE 10

The catalyst was 181 ppm. of triethyloxonium tetrafluoborate. The cumene hydroperoxide solution rose to 67° C. and in 50 minutes the product was analyzed. Analysis showed a selectivity of 92 percent to phenol, 2 percent to alpha-methylstyrene, 4 percent to acetophenone and 2 percent to dimethylbenzyl alcohol.

EXAMPLE 11

In this experiment 450 ppm. of triethyloxonium hexafluorophosphate was used. The cumene hydroperoxide solution rose to a maximum temperature of 97° C. in five minutes. Analysis of the product mixture showed a selectivity of 87 percent to phenol, 11 percent to alpha-methylstyrene and 2 percent to acetophenone.

EXAMPLE 12

The catalyst was 580 ppm. of triethyloxonium hexachlorostibnate. Analysis after 30 minutes and a maximum temperature of 80° C. showed a selectivity of the cumene hydroperoxide to phenol of 77 percent, to alpha-methylstyrene of 12 percent, to acetophenone of 6 percent and to dimethylbenzyl alcohol of 4 percent.

It is to be understood that the above disclosure is by way of example and that numerous modifications and variations are available to those of ordinary skill in the art without departing from the true spirit and scope of the invention.

We claim:

1. The method for cleaving cumene hydroperoxide at high selectivity to phenol and acetone which comprises contacting a solution comprising about 0.1 to about 20 weight percent cumene hydroperoxide with a catalytic amount of a salt comprising an organic cation selected from triphenylcarbonium, tropylium and tri(lower)alkyl oxonium and an inorganic anion selected from tetrafluoborate, hexafluorophosphate, hexachlorostibnate and hexafluoroarsenate at a temperature between about 25 and about 110° C.

2. The method for cleaving cumene hydroperoxide at high selectivity to phenol and acetone in accordance with claim 1 in which the catalyst is present in an amount between about 20 ppm. and about one weight percent.

3. The method for cleaving cumene hydroperoxide at high selectivity to phenol and acetone in accordance with claim 1 in which the solution comprises between about one and about five weight percent cumene hydroperoxide.

4. The method for cleaving cumene hydroperoxide at high selectivity to phenol and acetone in accordance with claim 1 in which the solution comprises phenol and acetone in a mol ratio between about 1:1 and about 1:10.

5. The method for cleaving cumene hydroperoxide at high selectivity to phenol and acetone in accordance with claim 1 in which the temperature is maintained between about 60 and about 80° C. by reflux of the acetone.

6. The method for cleaving cumene hydroperoxide at high selectivity to phenol and acetone in accordance with claim 1 in which there is between about 500 ppm. and about 0.5 weight percent of the catalyst.

7. The method for cleaving cumene hydroperoxide at high selectivity to phenol and acetone in accordance with claim 1 in which the catalyst is triphenylcarbonium tetrafluoborate.

8. The method for cleaving cumene hydroperoxide at high selectivity to phenol and acetone in accordance with claim 1 in which the catalyst is tropylium tetrafluoborate.

9. The method for cleaving cumene hydroperoxide at high selectivity to phenol and acetone in accordance with claim 1 in which the catalyst is triethyloxonium tetrafluoborate.

10. The method for cleaving cumene hydroperoxide at high selectivity to phenol and acetone in accordance with claim 1 in which the catalyst is triphenylcarbonium hexafluoroarsenate.

11. The method for cleaving cumene hydroperoxide at high selectivity to phenol and acetone in accordance with claim 1 in which the catalyst is triethyloxonium hexafluorophosphate.